(12) United States Patent
Hirsh et al.

(10) Patent No.: US 9,044,398 B2
(45) Date of Patent: *Jun. 2, 2015

(54) ABUSE-DETERRENT PHARMACEUTICAL COMPOSITIONS OF OPIODS AND OTHER DRUGS

(75) Inventors: Jane Hirsh, Wellesley, MA (US); Alexander M. Klibanov, Newton, MA (US); Timothy M. Swager, Newton, MA (US); Stephen L. Buchwald, Newton, MA (US); Whe Yong Lo, Canton, MA (US); Alison Fleming, Marshfield, MA (US); Roman V. Rariy, Allston, MA (US)

(73) Assignee: Collegium Pharmaceutical, Inc., Canton, MA (US)

( * ) Notice: Subject to any disclaimer, the term of this patent is extended or adjusted under 35 U.S.C. 154(b) by 0 days.
This patent is subject to a terminal disclaimer.

(21) Appl. No.: 13/551,455

(22) Filed: Jul. 17, 2012

(65) Prior Publication Data
US 2013/0045960 A1    Feb. 21, 2013

Related U.S. Application Data

(60) Continuation of application No. 12/112,993, filed on Apr. 30, 2008, now abandoned, which is a division of application No. 10/614,866, filed on Jul. 7, 2003, now Pat. No. 7,399,488.

(Continued)

(51) Int. Cl.
*A61K 9/14* (2006.01)
*A61K 9/42* (2006.01)
(Continued)

(52) U.S. Cl.
CPC .............. *A61K 9/1617* (2013.01); *A61K 47/12* (2013.01); *A61K 9/4858* (2013.01); *A61K 31/20* (2013.01); *A61K 9/145* (2013.01); *A61K 9/5052* (2013.01); *A61K 9/5084* (2013.01); *A61K 31/485* (2013.01)

(58) Field of Classification Search
CPC ..... A61K 9/145; A61K 9/4858; A61K 31/20; A61K 31/485; A61K 47/12
See application file for complete search history.

(56) References Cited

U.S. PATENT DOCUMENTS

| 3,015,128 A | 1/1962 | Somerville, Jr. |
| 3,336,200 A | 8/1967 | Krause et al. |

(Continued)

FOREIGN PATENT DOCUMENTS

| EP | 0253104 A1 | 1/1988 |
| EP | 0375063 A1 | 6/1990 |

(Continued)

OTHER PUBLICATIONS

Cortesi, et al., "Sugar cross-linked gelatin for controlled release: microspheres and disks," Biomaterials 19:1641-1649 (1998).

(Continued)

*Primary Examiner* — Lakshmi Channavajjala
(74) *Attorney, Agent, or Firm* — Cooley LLP

(57) ABSTRACT

An abuse-deterrent pharmaceutical composition has been developed to reduce the likelihood of improper administration of drugs, especially drugs such as opiods. In the preferred embodiment, a drug is modified to increase its lipophilicity. In preferred embodiments the modified drug is homogeneously dispersed within microparticles composed of a material that is either slowly soluble or not soluble in water. The abuse-deterrent composition retards the release of drug, even if the physical integrity of the formulation is compromised (for example, by chopping with a blade or crushing) and the resulting material is placed in water, snorted, or swallowed. However, when administered as directed, the drug is slowly released from the composition as the composition is broken down or dissolved gradually within the GI tract by a combination of enzymatic degradation, surfactant action of bile acids, and mechanical erosion.

11 Claims, 1 Drawing Sheet

Related U.S. Application Data

(60) Provisional application No. 60/463,514, filed on Apr. 15, 2003, provisional application No. 60/443,226, filed on Jan. 28, 2003, provisional application No. 60/436,523, filed on Dec. 23, 2002, provisional application No. 60/393,876, filed on Jul. 5, 2002, provisional application No. 60/463,518, filed on Apr. 15, 2003.

(51) Int. Cl.
| | | |
|---|---|---|
| A61K 31/20 | (2006.01) | |
| A61K 31/485 | (2006.01) | |
| A61K 9/16 | (2006.01) | |
| A61K 47/12 | (2006.01) | |
| A61K 9/48 | (2006.01) | |
| A61K 9/50 | (2006.01) | |

(56) References Cited

U.S. PATENT DOCUMENTS

| | | |
|---|---|---|
| 3,773,955 A | 11/1973 | Pachter et al. |
| 3,966,940 A | 6/1976 | Pachter et al. |
| 3,980,766 A | 9/1976 | Shaw et al. |
| 4,070,494 A | 1/1978 | Hoffmeister et al. |
| 4,457,933 A | 7/1984 | Gordon et al. |
| 4,569,937 A | 2/1986 | Baker et al. |
| 4,675,140 A | 6/1987 | Sparks et al. |
| 4,722,941 A | 2/1988 | Eckert et al. |
| 4,861,598 A | 8/1989 | Oshlack |
| 4,869,904 A | 9/1989 | Uekama et al. |
| 5,190,947 A | 3/1993 | Riess et al. |
| 5,356,467 A | 10/1994 | Oshlack et al. |
| 5,460,826 A | 10/1995 | Merrill et al. |
| 5,508,042 A | 4/1996 | Oshlack et al. |
| 5,756,483 A | 5/1998 | Merkus |
| 5,849,240 A | 12/1998 | Miller et al. |
| 5,891,471 A | 4/1999 | Miller et al. |
| 5,914,129 A | 6/1999 | Mauskop |
| 5,952,005 A | 9/1999 | Olsson et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 6,048,736 A | 4/2000 | Kosak |
| 6,068,855 A | 5/2000 | Leslie et al. |
| 6,103,261 A | 8/2000 | Chasin et al. |
| 6,156,764 A | 12/2000 | Asmussen et al. |
| 6,162,467 A | 12/2000 | Miller et al. |
| 6,255,502 B1 | 7/2001 | Penkler et al. |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,309,668 B1 | 10/2001 | Bastin et al. |
| 6,310,072 B1 | 10/2001 | Smith et al. |
| 6,328,979 B1 | 12/2001 | Yamashita et al. |
| 6,335,033 B2 | 1/2002 | Oshlack et al. |
| 6,375,957 B1 | 4/2002 | Kaiko et al. |
| 6,379,707 B2 | 4/2002 | Vladyka, Jr. et al. |
| 6,475,494 B2 | 11/2002 | Kaiko et al. |
| 6,692,767 B2 | 2/2004 | Burnside et al. |
| 6,696,088 B2 | 2/2004 | Oshlack et al. |
| 6,706,281 B2 | 3/2004 | Oshlack et al. |
| 6,723,343 B2 | 4/2004 | Kugelmann |
| 6,743,442 B2 | 6/2004 | Oshlack et al. |
| 6,919,372 B1 | 7/2005 | Yamashita et al. |
| 7,011,846 B2 | 3/2006 | Shojaei et al. |
| 7,261,529 B2 | 8/2007 | Persyn et al. |
| 7,399,488 B2 | 7/2008 | Hirsh et al. |
| 7,670,612 B2 | 3/2010 | Miller |
| 7,771,707 B2 | 8/2010 | Hirsh et al. |
| 8,449,909 B2 * | 5/2013 | Hirsh et al. ............ 424/458 |
| 8,557,291 B2 | 10/2013 | Rariy et al. |
| 2001/0006650 A1 | 7/2001 | Burnside et al. |
| 2001/0036476 A1 | 11/2001 | Oshlack et al. |
| 2002/0032166 A1 | 3/2002 | Shefter et al. |
| 2002/0081333 A1 | 6/2002 | Oshlack et al. |
| 2003/0059397 A1 | 3/2003 | Hughes |
| 2003/0064099 A1 | 4/2003 | Oshlack et al. |
| 2004/0052731 A1 | 3/2004 | Hirsh et al. |
| 2004/0062778 A1 | 4/2004 | Shefer et al. |
| 2005/0013862 A1 | 1/2005 | Tobyn et al. |
| 2005/0181050 A1 | 8/2005 | Hirsh et al. |
| 2005/0281748 A1 | 12/2005 | Hirsh et al. |
| 2006/0104909 A1 | 5/2006 | Vaghefi et al. |
| 2008/0199530 A1 | 8/2008 | Hirsh et al. |
| 2008/0260819 A1 | 10/2008 | Fleming et al. |
| 2009/0297617 A1 | 12/2009 | Rariy et al. |
| 2010/0260834 A1 | 10/2010 | Hirsh et al. |
| 2011/0142943 A1 | 6/2011 | Rariy et al. |
| 2013/0310413 A1 | 11/2013 | Hirsh et al. |

FOREIGN PATENT DOCUMENTS

| | | |
|---|---|---|
| EP | 0578231 AI | 1/1994 |
| EP | 0647448 A1 | 4/1995 |
| GB | 1513166 | 6/1978 |
| WO | WO 93/10765 A1 | 6/1993 |
| WO | WO 95/20947 A1 | 8/1995 |
| WO | WO 97/14438 A1 | 4/1997 |
| WO | WO 97/49402 A1 | 12/1997 |
| WO | WO 98/18827 A1 | 5/1998 |
| WO | WO 00/50007 A1 | 8/2000 |
| WO | WO 01/08661 A2 | 2/2001 |
| WO | WO 01/58447 A1 | 8/2001 |
| WO | WO 01/72338 A1 | 10/2001 |
| WO | WO 03/004029 A1 | 1/2003 |
| WO | WO 2004/075877 A1 | 9/2004 |

OTHER PUBLICATIONS

Gennaro, ed., Remington: The Science and Practice of Pharmacology, 20th ed., Lipincott: Baltimore, MD, pp. 704-706 (2000).

Abuse and Mental Health Services Administration, "Results from the 2004 National Survey on Drug Use and Health: National Findings," pp. 1-310 (2005).

Nakmura, et al., "Development of an oral sustained release drug delivery system utilizing pH-dependent swelling of carboxyvinyl polymer", J. Control. Rel., 111:309-319 (2006).

Rodriguez et al., "Description and preliminary evaluation of a new ultrasonic atomizer for spray-congealing processes," Int. J. Pharm. 183(2):133-143 (1999).

"Supplementary European Search Report," 7 pages, EP appl. No. 03763229.6 (Sep. 19, 2008).

"International Preliminary Report on Patentability," 6 pages, PCT appl. No. PCT/US2005/020588 (Oct. 2, 2006).

"International Search Report," 4 pages, PCT appl. No. PCT/US2005/020588 (Sep. 9, 2005).

"Written Opinion of the International Searching Authority," 6 pages, PCT appl. No. PCT/US2005/020588 (Sep. 9, 2005).

"Written Opinion," 4 pages, PCT appl. No. PCT/US03/21095 (Jun. 20, 2004).

"International Search Report," 2 pages, PCT appl. No. PCT/US03/21095 (Nov. 6, 2003).

"International Preliminary Report on Patentability," 3 pages, PCT appl. No. PCT/US03/21095 (Apr. 25, 2005).

"Castor oil, hydrogenated," European Pharmacopoeia V.5, p. 1197-1198 (2005).

Bush et al., "A comparison of a theophylline-ephedrine combination with terbutaline," Ann. Allergy 41:13-17 (1978) abstract.

Chemical Abstract Society (CAS), Properties for HPMC (CAS reg. No. 9004-65-3) accessed Jun. 29, 2013.

Choi et al., "Hydrophobic ion pair formation between leuprolide and sodium oleate for sustained release from biodegradable polymeric microspheres," Int. J. Pharm. 203:193-202 (2000).

Lan et al., "Studies on the Synthesis and Thermal Properties of Copoly(L-lactic acid/glycolic acid) by Direct Melt Polycondensation," J. Appl. Polymer Sci. 92:2163-2168 (2004).

Raffin et al., "Sodium pantoprazole-loaded enteric microparticles prepared by spray drying: Effect of the scale of production and process validation," Int. J. Pharm. 324:10-18 (2006).

(56) References Cited

OTHER PUBLICATIONS

Redden et al., "In vitro hydrolysis of polyunsaturated fatty acid N-acyloxymethyl derivatives of theophylline," Int. J. Pharm. 165:87-96 (1998).

Takka et al., "Effect of anionic polymers on the release of propanol hydrochloride from matrix tablets," Eur. J. Pharm. Biopharm. 52:75-82 (2001).

U.S. Appl. No. 14/054,513, filed Oct. 15, 2013.

U.S. Appl. No. 14/147,088, filed Jan. 3, 2014.

* cited by examiner

ABUSE-DETERRENT PHARMACEUTICAL COMPOSITIONS OF OPIODS AND OTHER DRUGS

This application is Continuation of U.S application Ser. No. 12/112,993 filed Apr. 30,2008, which is a Divisional of U.S. application Ser. No. 10/614,866 filed Jul. 7, 2002, which claims the benefit of U.S. Ser. No. 60/393,876 filed Jul. 5, 2002 entitled "Abuse-Resistant Formulations of Oxycontin and Other Drugs" by Alexander M. Klibanov, Stephen L. Buchwald, Timothy M. Swager, and Whe-Yong Lo; U.S. Ser. No. 60/436,523 filed Dec. 23, 2002 by Alison B. Fleming, Roman V. Rariy, Alexander M. Klibanov, Whe-Yong Lo, and Jane Hirsh; U.S. Ser. No. 60/443,226 filed Jan. 28, 2003 by Jane Hirsh, Alison B. Fleming, Alexander M. Klibanov, and Whe-Yong Lo; U.S. Ser. No. 60/463,514 filed Apr. 15, 2003 by Jane C. Hirsh, Alison B. Fleming, Roman V. Rariy, Stephen L. Buchwald, and Timothy M. Swager; and U.S. Ser. No. 60/463,518 filed Apr. 15, 2003 by Jane C. Hirsh, Alison B. Fleming and Roman V. Rariy, each of which is herein incorporated by reference in its entirety for all purposes.

BACKGROUND OF THE INVENTION

The present invention is generally in the field of pharmaceutical compositions, and specifically relates to compositions that are designed to reduce the potential for improper administration of drugs that are subject to abuse.

Oxycodone, morphine, and other opiod analgesics are successful and therapeutically useful medications, e.g., as pain killers, when administered orally. Unfortunately, they also pose a severe threat for willful abuse due to their ability to alter mood and/or cause a sense of euphoria. Currently available sustained release formulations of such drugs, which contain a relatively large amount of drug meant to be released from the formulation over an extended time period, are particularly attractive to abusers since the sustained release action can be destroyed by crushing or grinding the formulation. The resulting material (ie, the crushed formulation) can no longer control the release of drug. Depending on the drug, abusers can then (1) snort the material, (2) swallow the material or (3) dissolve the material in water and subsequently inject it intravenously. The dose of drug contained in the formulation is thus absorbed immediately through the nasal or GI mucosa (for snorting or swallowing, respectively) or is administered in a bolus to the systemic circulation (for IV injection). These abuse methods result in the rapid bioavailability of relatively high doses of drug, giving the abuser a "high". Since relatively simple methods (crushing, grinding, chewing and/or dissolution in water) can be used to transform such formulations into an abusable form, they provide virtually no deterrent to a potential abuser.

For example, the FDA recently strengthened the warnings and precautions sections in the labeling of OxyContin® (oxycodone HCl controlled-release) Tablets, a narcotic drug approved for the treatment of moderate to severe pain, because of continuing reports of abuse and diversion. OxyContin® contains oxycodone HCl (available in 10, 20, 40 and 80 mg strengths), an opioid agonist with an addiction potential similar to that of morphine. Opioid agonists are substances that act by attaching to specific proteins called opioid receptors, which are found in the brain, spinal cord, and gastrointestinal tract. When these drugs attach to certain opioid receptors in the brain and spinal cord they can effectively block the transmission of pain messages to the brain. OxyContin® is supplied in a controlled-release dosage form and is intended to provide up to 12 hours of relief from moderate to severe pain. The warning specifically states that the tablet must be taken whole and only by mouth. When the tablet is chewed or crushed and its contents are swallowed, snorted into the nostrils or dissolved and subsequently injected intravenously, the controlled release mechanism is destroyed and a potentially lethal dose of oxycodone becomes bioavailable.

In recent years, there have been numerous reports of Oxycodone diversion and abuse in several states. For example, DEA's Office of Diversion Control reported 700 OxyContin® thefts in the US between January 2000 and June 2001. Some of these reported cases have been associated with serious consequences including death.

Oxycodone is a controlled substance in Schedule II of the Controlled Substances Act (CSA), which is administered by the Drug Enforcement Administration (DEA). Despite the fact that Schedule II provides the maximum amount of control possible under the CSA for approved drug products, in practice it is difficult for law enforcement agencies to control the diversion or misuse of legitimate prescriptions. Although abuse, misuse, and diversion are potential problems for all opioids, including Oxycodone, opioids are a very important part of the medical armamentarium for the management of pain when used appropriately under the careful supervision of a physician.

Currently available formulations for such drugs are designed for oral administration but do not include mechanisms to prevent or retard improper methods of administration such as chewing, injection and snorting. This represents a serious problem given the large number of legitimate prescriptions written in the US; for example, the medical use of opiods within the US increased 400% from 1996 to 2000. The problems with abuse are significant and longstanding, and efforts to design new abuse-resistant or abuse-deterrent formulations have been largely unsuccessful. U.S. Pat. Nos. 3,980,766, 4,070,494 and 6,309,668 describe formulations designed to prevent the injection of compositions meant for oral administration. U.S. Pat. No. 3,980,766 describes the incorporation of an ingestible solid which causes a rapid increase in viscosity upon concentration of an aqueous solution thereof. U.S. Pat. No. 4,070,494 describes the incorporation of a non-toxic, water gelable material in an amount sufficient to render the drug resistant to aqueous extraction. U.S. Pat. No. 6,309,668 describes a tablet for oral administration containing two or more layers comprising one or more drugs and one or more gelling agents within separate layers of the tablet.

The resulting tablet forms a gel when combined with the volume of water necessary to dissolve the drug; this formulation thus reduces the extractability of the drug from the tablet. It should be noted that although these compositions preclude abuse by injections, this approach fails to prevent abuse by crushing and swallowing or snorting the formulation, which are commonly reported methods of abuse associated with OxyContin®.

U.S. Pat. Nos. 3,773,955 and 3,966,940 describe formulations containing a combination of opiod agonists and antagonists, in which the antagonist does not block the therapeutic effect when the admixture is administered orally, but which does not produce analgesia, euphoria or physical dependence when administered parenterally by an abuser. U.S. Pat. No. 4,457,933 describes a method for decreasing both the oral and parenteral abuse potential of strong analgetic agents by combining an analgesic dose of the analgetic agent with an antagonist in specific, relatively narrow ratios. U.S. U.S. Pat. Nos. 6,277,384, 6,375,957 and 6,475,494 describe oral dosage forms including a combination of an orally active opiod agonist and an orally active opiod antagonist in a ratio that, when delivered orally, is analgesically effective but that is aversive in a physically dependent subject. While such a formulation may be successful in deterring abuse, it also has the potential to produce adverse effects in legitimate patients.

It is therefore an object of the present invention to provide a pharmaceutical composition that significantly reduces the potential for improper administration or use of drugs but which, when administered as directed, is capable of delivering a therapeutically effective dose.

SUMMARY OF THE INVENTION

An abuse-deterrent pharmaceutical composition and the method of making and using the composition have been developed. The composition can be used to reduce the likelihood of improper administration of drugs, especially drugs such as oxycodone. The technology is useful for a number of other drugs where sustained release oral delivery is desired, and there is the potential for abuse if the drug dose is made immediately available for nasal, IV or oral administration. In the preferred embodiment, the drug is chemically modified to increase its lipophilicity. In other embodiments, the formulation contains lipophilic or water-insoluble materials or is made using a process which increases the lipophilicity and/or water-insolubility of the composition.

The abuse-deterrent composition retards the release of drug, even if the physical integrity of the dosage form is compromised (for example, by chopping with a blade or crushing) and the resulting material is placed in water, snorted, or swallowed. The composition thus provides a deterrent to common methods of improper administration including IV injection of drug dissolved in water and nasal or oral administration of the crushed formulation since drug will not be immediately released from the formulation. However, when administered as directed, the drug is slowly released (typically over a period of 4-18 hours) from the composition as the composition is broken down or dissolved gradually within the GI tract by a combination of enzymatic degradation, surfactant action of bile acids, and mechanical erosion.

In some embodiments, the individual drug-containing microparticles or drug particles are coated with one or more independent coating layers. At least one of the coating materials is water-insoluble and preferably organic solvent-insoluble, but enzymatically degradable. The components of the resulting coated microparticles are not mutually soluble in water, organic solvents, or any combination thereof, so that in vitro degradation of the formulation will require more than one step. Hence the drug is not easily extractable from such a formulation by conventional chemical means. In contrast, when administered to the gastrointestinal tract via swallowing, the drug gradually will be released from the coated microparticles as a consequence of enzymatic degradation, surfactant action of bile acids and mechanical erosion within the GI tract.

The pharmaceutical composition, when administered orally, results in a desired drug release profile. Such a release profile provides a therapeutic effect for an extended period of time, typically from 6 to 24 hours. Additional compositions are provided which achieve a small immediate dose that precedes the sustained release of drug. The compositions disclosed herein may optionally comprise a drug having no appreciable abuse potential.

DETAILED DESCRIPTION OF THE INVENTION

Figure 1A:
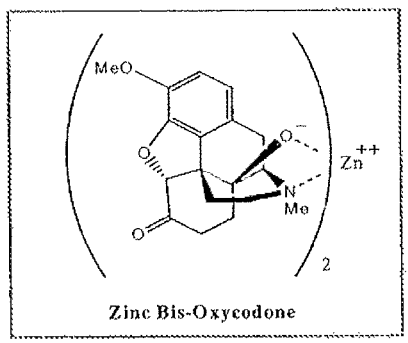
FIG. 1A is a structural schematic of zinc bis-oxycodone.

Disclosed herein are an abuse-deterrent pharmaceutical composition and the method of making and using the composition.

I. Compositions

As used herein, "composition" refers to the drug dosage unit for administration to a patient. This may also be used in reference solely to the active ingredient, or to the formulation containing the active ingredient.

The currently available sustained release dosage forms containing narcotic analgesics and other drugs are subject to misuse, in part, because mechanical destruction of the dosage form exposes the encapsulated drug and allows for immediate dissolution of the drug into aqueous media. Two properties of the dosage form that contribute to this outcome are (1) the ease with which drug is exposed to the extraction media and (2) the high water solubility of the drug salt form.

In the composition disclosed herein, one or both of these properties are altered in order to achieve an abuse-deterrent composition. Specifically, in the preferred embodiment, the drug is modified to increase its lipophilicity and, in additional preferred embodiments, is then homogeneously dispersed within a material that is either slowly soluble or not soluble in water and subsequently formulated into microparticles. The drug may be present in the form of discrete particles or may be partially or fully dispersed in the carrier material on a molecular level.

The terms "abuse-deterrent composition" or "abuse-deterrent formulation" are used interchangeably herein to refer to compositions that reduce the potential for improper administration of drugs but that deliver a therapeutically effective dose when administered as directed. Improper administration includes tampering with the dosage form and/or administering the drug by any route other than instructed. For example, for a tablet or capsule, methods of tampering with the dosage form may include, but are not limited to, breaking, crushing, grinding, chewing and/or dissolving the tablet or the contents of the capsule. For oral administration, improper administration includes administering the drug by any route other than via swallowing.

The abuse deterrent composition preferably comprises a drug modified to increase its lipophilicity. In other preferred embodiments, the drug is homogeneously dispersed within microparticles composed of a material that is either slowly soluble in water or water insoluble. The compositions slow the release of drug if the dosage form is chopped or crushed and the resulting material is placed in water, snorted, or swallowed since most of the drug will remain associated with or entrapped within portions of the core material of the microparticles. In some embodiments the drug containing microparticles or individual drug particles are coated with one or more coating layers, where at least one coating is water insoluble and preferably organic solvent insoluble, but enzymatically degradable. The components of the resulting coated microparticles are not mutually soluble in water, organic solvents, or any combination thereof, such that no one solvent or enzyme solution is capable of dissolving the formulation in its entirety in vitro. It follows that extraction of the drug from the formulation cannot be carried out in one step. However, when administered as directed, the drug is slowly released from the formulation since it is eroded within the environment of the gastrointestinal tract.

A. Drugs to be Formulated

There are many drugs that it is desirable to deliver using the compositions described herein. The Controlled Substances Act (CSA), Title 11 of the Comprehensive Drug Abuse Prevention and Control Act of 1970, places all substances that are regulated under existing federal law into one of five schedules based upon the substance's medicinal value, harmfulness, and potential for abuse or addiction. Drugs that are preferred include those classified as Schedule II, III, IV and V drugs. Drugs that are most preferable include those, like oxycodone, that are currently formulated as sustained or controlled release compositions, where drug release is intended to occur over a prolonged period of time through the gastrointestinal tract, and immediate or burst release, for example, by inhalation or injection, is undesirable. As used herein, drugs prone to abuse refer to controlled substance specified as schedule II, II, IV and V drugs.

The terms "drug", "active agent", and "pharmacologically active agent" are used interchangeably herein to refer to a chemical compound that induces a desired pharmacological, physiological effect. The terms also encompass pharmaceutically acceptable derivatives of those active agents specifically mentioned herein, including, but not limited to, salts, solvates, hydrates, complexes with one or more molecules, prodrugs, active metabolites, analogs, and the like. When the terms "active agent", "pharmacologically active agent" and "drug" are used, or when a particular drug, such as oxycodone, is identified, it is to be understood as including the active agent per se as well as pharmaceutically acceptable salts, solvates, hydrates, complexes with one or more molecules, prodrugs, active metabolites, and analogs.

Examples of preferred drugs include, 1-phenylcyclohexylamine, 1-piperidinocyclohexanecarbonitrile, alfentanil, alphacetylmethadol, alphaprodine, alprazolam, amobarbital, amphetamine, anileridine, apomorphine, aprobarbital, barbital, barbituric acid derivative, bemidone, benzoylecgonine, benzphetamine, betacetylmethadol, betaprodine, beziramide, bromazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecgonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethadol, levomethadone, levomethadyl acetate, levomethorpban, levorphanol, lofentanil, loperamide, loprazolam, lorazepam, lormetazepam, lysergic acid, lysergic acid amide, mazindol, medazepam, mefenorex, meperidine, meptazinol, metazocine, methadone, methamphetamine, methohexital, methotrimeprazine, methyldihydromorphinone, methylphenidate, methylphenobarbital, metopon, morphine, nabilone, nalbuphine, nalbupine, nalorphine, narceine, nefopam, nicomorphine, nimetazepam, nitrazepam, nordiazepam, normethadone, normorphine, oxazepam, oxazolam, oxycodone, oxymorphone, pentazocine, pentobarbital, phenadoxone, phenazocine, phencyclidine, phendimetrazine, phenmetrazine, phenerdine, piminodine, prodilidine, properidine, propoxyphene, racemethorphan, racemorphan, racemoramide, remifentanil, secobarbital, sufentanil, talbutal, thebaine, thiamylal, thiopental, tramadol, trimeperidine, and vinbarbital.

In addition to the compounds above, the following scheduled drugs may be incorporated into the composition: allobarbitone, alprazolam, amylobarbitone, aprobarbital, barbital, barbitone, benzphetamine, brallobarbital, bromazepam, brotizolam, buspirone, butalbital, butobarbitone, butorphanol, camazepam, captodiame, carbromal, carfentanil, carpipramine, cathine, chloral, chloral betaine, chloral hydrate, chloralose, chlordiazepoxide, chlorhexadol, chlormethiazole edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, enciprazine, estazolam, ethyl loflazepate, etizolam, febarhamate, fencamfamin, fenfluramine, fenproporex, fluanisone, fludiazepam, flunitraam, flunitrazepam, flurazepam, flutoprazepam, gepirone, glutethimide, halazepam, haloxazolam, hexobarbitone, ibomal, ipsapirone, ketazolam, loprazolam mesylate, lorazepam, lormetazepam, mazindol, mebutamate, medazepam, mefenorex, mephobarbital, meprobamate, metaclazepam, methaqualone, methohexital, methylpentynol, methylphenobarbital, midazolam, milazolam, morphine, nimetazepam, nitrazepam, nordiazepam, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibarbal, quazepam, quinalbaritone, secobarbital, secbutobarbitone, sibutramine, temazepam, tetrazeparn, triazolam, triclofos, zalepan, zaleplon, zolazepam, zolpidem, and zopiclone. Certain compounds described herein may exist in particular geometric or stereoisomeric forms. The composition disclosed herein contemplates all such compounds, including cis- and trans-isomers, R- and S-enantiomers, diastereomers, (D)-isomers, (L)-isomers, the racemic mixtures thereof, compounds of different spacial conformations, and other mixtures thereof, as failing within the scope of the invention. Additional asymmetric carbon atoms may be present in a substituent such as an alkyl group. All such isomers, as well as mixtures thereof, are intended to be included in this invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704, the disclosure of which is hereby incorporated by reference.

Optionally, the composition described herein can further include a drug having no appreciable abuse potential.

B. Drug Solubility Modification

In preferred embodiments, the solubility characteristics of a drug are altered prior to incorporation into the formulation. Modification of the drug to produce a more lipophilic derivative serves to reduce the water solubility of the drug and thus reduces the aqueous extractability. Furthermore, if the drug is made more lipophilic, it can be solubilized in a molten fatty substance or wax like mixture, rather than physically dispersed in a particulate form. Solubilisation of drug enhances the abuse-deterrent properties of microparticles formulated from the mixture as it is difficult to extract drug from an intimately dispersed composition.

The terms "lipophilic derivative" and "hpophililic drug derivative", as used herein, refer to derivatives of the drug that are less soluble in water than the most soluble salt of the drug. The most soluble salt being selected from either drug alkaline metal salts (for acidic drugs) or salts of the drug with inorganic acids (for basic drugs). The examples of the latter include but are not limited to hydrohalates, sulfates, and nitrates.

Some of the methods that can be used to alter the drug's lipophilicity are outlined below. It is understood that two or more approaches can be combined to achieve a desired solubility profile.

Methods for Increasing Lipophilicity

In one embodiment, drug is made more lipophilic by eliminating or reducing the overall charge of the drug molecule. For example, for a basic drug, a water soluble salt (such as hydrochloride, sulfate, or maleate) can be converted to a free base using techniques known in the art. Correspondingly, in the case of an acidic drug, a water soluble salt (such sodium, potassium, or the like) can be converted to a free acid.

In another embodiment, the drug's lipophilicity is increased by forming a salt between a drug molecule and a charged lipophilic compound. In this case the lipophilicity of the resulting salt can be manipulated by varying the lipophilicity of the counter-ion. In general lipophilic acids or amines with chain lengths between $C_5$-$C_{30}$ are lipophilic counter-ion candidates. Some specific examples include, but are not limited to, linoleic acid, octanoic acid, lauric acid, stearic acid, palmitic acid, oleic acid, octyl amine, lauryl amine, stearyl amine, palmityl amine, linoleyl amine, and oleyl amine. Other salts which may increase lipophilicity and, hence, lipid solubility relative to the parent drug compound include, but are not limited to, pectinate, tannate, phytate, salicylate, saccharinate, acesulfamate, gallate, and terephthalate salts.

In yet another embodiment the lipophilicity of the drug is increased by forming a stable complex between a drug molecule (either charged or uncharged) and a metal cation such as zinc, magnesium, calcium, bismuth or the like. This complex may consist of one or more drug molecules, one or more metal cations, and, optionally, one or more lipophilic charged species. The aforementioned charged lipophilic species are incorporated into the complex if necessary to bring the charge of the final complex to zero and increase its overall lipophilicity. In general lipophilic acids or amines with chain lengths between $C_5$-$C_{30}$ are lipophilic counter-ion candidates. Examples of such complexes for a narcotic drug oxycodone are given in FIG. 1; a lipophilic drug complex may be composed of one or two oxycodone molecules, one $Zn^{2+}$ cation, and one or two stearate anions. It is understood by one skilled in the art that various metal cations as well as lipophilic counter-ions can he used to form complexes with an analogous structure, for example, oxymorphone.

In still a further embodiment, drug lipophilicity is increased via complexation with poorly water-soluble cyclodextrin. For example, ethylated beta-cyclodextrin has been shown to decrease aqueous solubility of complexed drug molecules.

In another embodiment, a drug is covalently modified to increase its lipophilicity. For example, a lipophilic compound can be covalently attached to a drug molecule via an ester or amide linkage. Such drug derivatives are cleaved in vivo, thus releasing the parent compound.

C. Drug Containing Microparticles

In preferred embodiments, drugs are formulated with a carrier material to form microparticles. As used herein, the term "microparticle" refers to a composition comprising a drug dispersed within a carrier material and "coated microparticle" refers to a composition comprising a drug containing microparticle or a drug particle coated with one or more coating layers of material. Microparticles and coated microparticles have a size range of 10 to 3000 microns in diameter.

Within microparticles, drug is preferably homogeneously dispersed in the form of fine particles within the carrier material. More preferably, drug is partially solubilized in molten carrier material or partially dissolved with the carrier material in a mutual solvent during the formulation of the microparticles. Most preferably, drug is completely solubilized in the molten carrier material or completely dissolved with the carrier material in a co-solvent during the formulation of the microparticles. This is accomplished through the selection of materials and the manner in which they are processed.

Carrier materials appropriate for the fabrication of drug containing microparticles are either slowly soluble in water or insoluble in water, but capable of degrading within the GI tract by means including enzymatic degradation, surfactant action of bile acids and mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the hydrophobic drug containing microparticles. To this end, rate-controlling (wicking) agents may be formulated along with the fats or waxes listed above. Examples of rate-controlling materials include certain starch derivatives (eg, waxy maltodextrin and drum dried corn starch), cellulose derivatives (eg, hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins which are water insoluble, such as zein, are preferred carrier materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Certain polymers may also be used as carrier materials in the formulation of drug containing microparticles. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as carrier materials for drug containing microparticles.

Encapsulation or incorporation of drug into carrier materials to produce drug containing microparticles can he achieved through known pharmaceutical formulation techniques. To create a composition that protects drug from exposure upon mechanical disruption (eg, grinding, chewing, or chopping), the drug is intimately dispersed within the carrier material. ID the case of formulation in fats, waxes or wax-like materials, the carrier material is heated above its melting temperature and the drug is added to form a mixture comprising drug particles suspended in the carrier material, drug dissolved in the carder material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", $20^{th}$ Edition, Jennaro et. Al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In addition to modification of the drug itself, processing conditions can be used to influence the dispersion of the drug within water-insoluble or slowly water soluble material. For example, in the case where the water in-soluble or slowly soluble material is melted and drug is fully or partially dissolved under stirring conditions, the temperature, agitation rate and time of processing will influence the degree of dissolution achieved. More specifically, a more homogeneous dispersion may be achieved with a higher temperature, faster stirring rate and longer processing time. Ultrasound can also be applied to the molten mixture to increase the degree of dispersion and/or the rate of dissolution of the drug.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

D. Coated Drug Containing Microparticles

In some embodiments, drug containing microparticles or drug particles are encapsulated within at least one water-insoluble enzymatically degradable material. In some instances the substrates of digestive enzymes are naturally water-insoluble and can be utilized in the formulation without further processing. Solid esters of fatty acids, which are hydrolyzed by lipases, can be spray coated onto microparticles or drug particles. Zein is an example of a naturally water-insoluble protein. It can be coated onto drug containing microparticles or, drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde, and formaldehyde), epoxy compounds, carbodiimides, and genipin. In addition to these cross-linking agents, oxidized and native sugars have been used to cross-link gelatin (Cortesi, R., et at, Biomaterials 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be. complexed via electrostatic interactions. Insoluble coatings can be formed on particles in this fashion. It should be noted that in many cases polysaccharides are broken down specifically by enzymes produced by bacteria within the colon.

In some cases a water-insoluble but enzymatically degradable coating comprising both a protein and a polysaccharide can be produced if the components are oppositely charged polyelectrolytes. Under the proper temperature, pH, and concentrations, the two polymers can interact through their opposite electrical charges and form a water-insoluble complex. If a core particle is present at the time the complex phase separates, it will be coated. For example, gelatin and gum arabic can be coated onto a core particle utilizing this process.

Optionally, the complex can be made irreversibly insoluble by subsequent cross-linking induced by chemical or physical means.

E. Dosage Forms

There are a number of drug compositions that meet the abuse deterrent criteria outlined above. In one embodiment a drug is homogeneously dispersed, in a fine particulate form, within a water-insoluble or slowly water soluble material and the mixture is formulated into microparticles. In another embodiment a drug is partially dissolved within a water-insoluble or slowly water soluble material during the manufacturing process, for example, by mixing at a temperature above the melting point of the carrier material, and the mixture is formulated into microparticles. In yet another embodiment a drug is fully dissolved within a water-insoluble or slowly water soluble material during the manufacturing process, for example, by mixing at a temperature above the melting point of the carrier material, and the mixture is formulated into microparticles. In still a further embodiment, the drug containing microparticles, where the drug is homogeneously dispersed in a particulate form, or has been partially or fully dissolved within the carrier material during the manufacturing process, are coated with one or more coatings to form coated microparticles. In a further embodiment, drug particles are coated directly with one or more coatings to form coated microparticles.

The microparticles, coated microparticles, or a mixture thereof are formed into a solid dosage form suitable for oral administration. For example, microparticles or coated microparticles can be incorporated into hard capsules, dispersed within a soft gelatin capsule, or combined with appropriate excipients and tableted by compression.

In some embodiments, the compositions are coated with an enteric coating. Enteric coatings known in the art are applied directly to the abuse-deterrent microparticle or coated microparticle compositions or are applied to the surface of a capsule or tablet comprising the abuse deterrent microparticle and/or coated microparticle compositions. Enteric coatings known in the art include, for example, acrylic polymers that are commercially available under the trade name EUDRAGIT®, cellulose acetate phthalate, hydroxypropylmethylcellulose phthalate, polyvinyl acetate phthalate, shellac, hydroxypropylmethylcellulose succinate, cellulose acetate trimelljate or mixtures thereof.

Dosage forms can include one or more drugs. When the dosage form includes two or more drugs they can be Scheduled drugs or can be a combination of Scheduled and non-Scheduled drugs. The drugs can be incorporated into separate microparticle compositions where the Scheduled drugs are incorporated into abuse deterrent microparticle compositions and the non-Scheduled drugs are incorporated into abuse deterrent microparticle compositions, sustained release compositions known in the art or immediate release compositions known in the art. The compositions comprising the different drugs are formulated into a single solid dosage form suitable for oral administration, for example, they can be incorporated into a gelatin capsule, or combined with appropriate excipients and compressed into a tablet form. Examples of non-scheduled drugs that may be included in dosage forms described herein include, but are not limited to, aspirin, acetaminophen, non-steroidal anti-inflammatory drugs, cyclooxygenase II inhibitors, N-methyl-D-aspartate receptor antagonists, glycine receptor antagonists, triptans, dextromethorphan, promethazine, fiorinal, guaifenesin, butalbital, and caffeine.

An immediate release dose can be incorporated into the formulation in several ways. Immediate release microparticles can be made utilizing standard methodologies and formulated along with abuse-deterrent microparticle and/or coated microparticle compositions in a suitable oral dosage form. Alternatively, a coating containing drug which is available for immediate release can be placed On a tablet comprising abuse-deterrent microparticle and/or coated microparticle compositions plus appropriate excipients. Additionally, an immediate dose of drug can be granulated or blended with rapidly dissolving excipients and subsequently compressed (1) as one layer of bi-layer tablets in which the abuse-deterrent deterrent microparticle and/or coated microparticle compositions are compressed as the other layer, or (2) as the outer layer of compression-coated tablets in which the abuse-deterrent microparticle and/or coated microparticle compositions are compressed as the inner core, or (3) into tablets in which abuse-deterrent microparticle and/or coated microparticle compositions are embedded.

In some embodiments, the immediate release portion of the dosage form comprises a lipophilic drug derivative. For example, salt derivatives or complexes that are insoluble at a neutral pH but dissociate, thereby releasing the parent compound, at an acidic pH are ideal for immediate release within the stomach. In the case of oxycodone some salts that may exhibit this property include, but are not limited to, the tannate, phthalate, salicylate, gallate, pectinate, phytate, saccharin ate, acesulfamate and terephthalate salts. Complexes of drug with one or more metal ions and, optionally, one or more lipophilic counter-ions (see, for example, FIG. 1) may also be used for immediate drug release. Use of salts or complexes in the immediate release portion of the dosage form reduces the abuse potential of the immediate release dose if the formulation is crushed and (1) snorted or (2) dissolved in water since these salts will be poorly soluble under these conditions. It is understood by the one of ordinary skill in the art that such salts or complexes may also be used to formulate an immediate release dosage form without a sustained release portion.

Additional mechanisms to reduce the potential for abuse can also be incorporated during the process of formulating tablets. For example, ingredients can be added to deter chewing or snorting of the final formulation. For example, an intensely bitter substance may deter chewing, while an intensely spicy ingredient, such as capsaicin, may deter snorting. The addition of a colored dye, which would stain the skin and mucosal surface of the nose following snorting may also serve to reduce this practice.

Optional excipients present in the oral dosage form comprising abuse deterrent microparticles or coated microparticles include, but are not limited to diluents, binders, lubricants, disintigrants, colorants, plasticizers and the like. Diluents, also termed "fillers," arc typically necessary to increase the bulk of a solid dosage form so that a practical size is provided for compression of tablets. Examples of diluents include cellulose, dry starch, microcrystalline cellulose, dicalcium phosphate, calcium sulfate, sodium chloride confectioner's sugar, compressible sugar, dextrates, dextrin, dextrose, sucrose, mannitol, powdered cellulose, sorbitol, and lactose. Binders are used to impart cohesive qualities powdered materials and can include materials such as starch, gelatin, sugars, natural and synthetic gums, polyethylene glycol, ethylcellulose, methylcellulose, hydroxypropylmethylcellulose, carboxymethylcellulose, waxes and polyvinyl pyrrolidone. Lubricants are used to facilitate tablet manufacture; examples of lubricants include talc, magnesium stearate, calcium stearate, hydrogenated vegetable oils stearic acid, sodium stearyl fumarate, sodium benzoate, sodium acetate, leucine, sodium oleate, sodium lauryl sulfate, magnesium lauryl sulfate and polyethylene glycol. Disintigrants can be added to pharmaceutical formulations in order to facilitate "breakup" or disintegration after administration. Materials used for this purpose include starches, clays, celluloses, aligns, gums, and cross-linked polymers. A plasticizer may be included in coating materials to alter their mechanical properties. Examples of plasticizers include benzyl benzoate, chlorobutanol, dibutyl sebacate, diethyl phthalate, glycerin, mineral oil, polyethylene glycol, sorbitol, triacetin, triethyl citrate, glycerol, etc. In addition to the additives above, coloring and flavoring agents may also be incorporated into the composition.

Optionally, the composition disclosed herein comprises materials wherein a combination of the materials is not soluble in water, organic solvent, or any combination thereof.

II. Methods of Administration

It is assumed that upon oral ingestion of the intact composition, drug is released as the formulation is gradually broken down or dissolved within the GI tract by a combination of enzymatic degradation, surfactant action of bile acids, and mechanical erosion. This is a result of the unique ability of the human digestive system to efficiently break down or solubilize a variety of materials. The process within the GI tract that results in the digestion of food and the absorption of nutrients is well known. Following mastication within the mouth, food passes into the stomach where it is mixed with digestive juices. This fluid contains the proteolytic enzyme pepsin which, following activation by the low pH within the stomach, begins the process of cleaving ingested proteins into smaller peptide fragments. Food then enters the small intestine in the form of macromolecular aggregates, where it is digested into molecules near or in a form capable of being absorbed. This digestion is accomplished through the action of various enzymes which are produced in the pancreas and flow into the upper portion of the large intestine, the duodenum. The enzymes synthesized in the pancreas include proteases, amylases and lipases; these enzymes are capable of breaking down proteins, starches and fats, respectively. The digestion of fats is further facilitated by the secretion of bile into the duodenum since bile salts, which contain both hydrophobic and hydrophilic portions, are capable of emulsifying lipids into minute droplets in order to increase the surface area available for digestion by lipases. The material which remains following passage through the small intestine enters the large intestine. Bacteria capable of breaking down carbohydrates not digested in the small intestine (such as cellulose) are present in large numbers this region of the digestive tract. Finally, in addition to microbial fermentation, the large intestine functions to absorb water and electrolytes and to form and store feces until they are excreted.

In addition to providing a deterrent to common methods of abuse/diversion, the formulation can provide a sustained release of drug over an extended time period. This is a natural consequence of the fact that, in the present formulation, drug is slowly released from a predominantly water-insoluble, hydrophobic matrix following the degradation of the matrix. The barrier components are degraded, for example, by enzymes, the surfactant action of bile acids and mechanical erosion.

In some embodiments, an immediate release of drug is achieved within the stomach in order to provide rapid therapeutic onset.

The pharmaceutical drug composition is administered orally. The appropriate dosage formulations can be obtained by calculation of the pharmacokinetics of the formulation, then adjusting using routine techniques to yield the appropriate drug levels based on the approved dosage forms. Any suitable amount of drug containing microparticles or coated microparticles can be included in the final formulation. The selection of a suitable amount of drug containing microparticles depends on the dosage desired and is readily determined by those skilled in the art.

In addition to oral administration, some embodiments may also be administered by other routes, including, but not limited to, rectal and nasal administration. Some embodiments may also be suitable for formulation as oral liquids.

The present composition and method of making and using the composition will be further understood by reference to the following non-limiting examples.

EXAMPLE 1

Preparation of Lipophilic Oxycodone Derivatives

A. Oxycodone Free Base

The free base of oxycodone was prepared from its hydrochloride salt by the following method: Oxycodone hydrochloride was dissolved in water and sodium carbonate was added in the amount required to neutralize hydrochloric acid. Methylene chloride was added in order to extract the formed oxycodone free base. The obtained organic layer was dried over sodium sulfate and methylene chloride was evaporated using rotary evaporator. The obtained oxycodone free base was purified by crystallization.

B. Zinc-bis-oxycodone

Zinc bis-oxycodone can be obtained in anhydrous media by reacting oxycodone free base with $Zn(Et)_2$ C. Zinc Oxycodone Stearate Zinc oxycodone stearate can be obtained in anhydrous media by reacting oxycodone free base with $Zn(Et)(C_{18}H_{35}O_2)$ D. Zinc Oxycodone Di-stearate Zinc-oxycodone di-stearate can be obtained by co-melting $Zn(C_{18}H_{35}O_2)_2$ and oxycodone free base.

Oxycodone Terephthalate

Figure 1B:
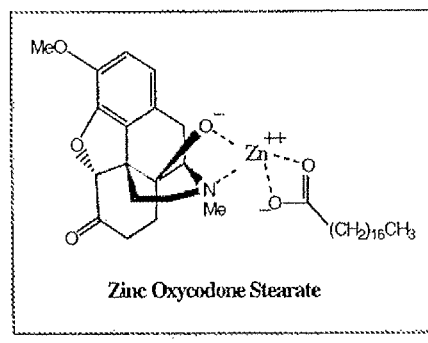
FIG. 1B is a structural schematic of zinc oxycodone stearate.
Figure 1C:
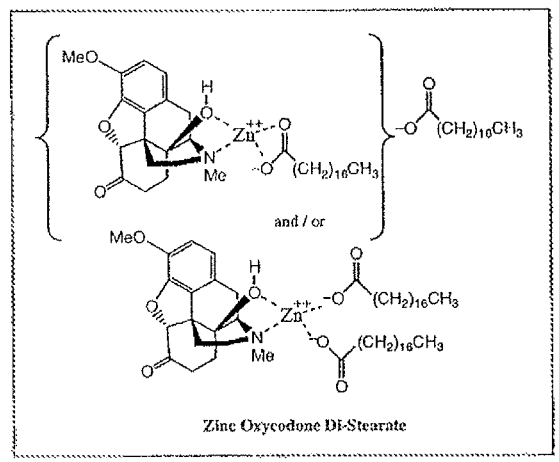
FIG. 1C is a structural schematic of zinc oxycodone di-stearate.

Oxycodone terephthalate is commercially available and can be used without further processing The structures of some representative oxycodone zinc complexes are shown in FIGS. 1A, 1B and 1C.

EXAMPLE 2

Preparation of Drug Containing Microparticles

The free base, salts or complexes from Example 1 are added to molten hydrogenated vegetable oil, mixed, extruded and spheronized to form drug containing microparticles.

EXAMPLE 3

Preparation of Coated Drug Containing Microparticles

The drug-containing particles from Example 2 are spray coated with zein in a fluidized bed apparatus.

EXAMPLE 4

Preparation of Capsules for Oral Administration

The drug containing microparticles from Example 2 and/or the coated microparticles from Example 3 are incorporated into standard gelatin capsules.

EXAMPLE 5

Preparation of Capsules for Oral Administration Containing a Dose of Drug for Immediate Release The drug containing microparticles from Example 2 and/or the coated microparticles from Example 3 are combined with immediate release drug particles, and incorporated into standard gelatin capsules.

We claim:

1. An abuse-deterrent pharmaceutical composition comprising a plurality of microparticles, where each microparticle comprises:
   a) a lipophilic drug derivative comprising a drug prone to abuse and a fatty acid, and
   b) one or more carrier material(s) selected from the group consisting of fats, fatty substances, waxes, wax-like substances, and mixtures thereof;
   wherein manufacturing said microparticles comprises solubilizing the lipophilic drug derivative in molten carrier material or dissolving the lipophilic drug derivative with the carrier material in a co-solvent; and
   wherein the release of a portion of incorporated drug is retarded when the physical integrity of the composition is compromised and the compromised composition is exposed to water.

2. The composition of claim 1 wherein the composition is a controlled-release pharmaceutical composition.

3. The composition of claim 1 wherein the drug prone to abuse is selected from the group consisting of 1-phenylcyclohexylamine, 1-piperidinocyclohexanecarbonitrile, alfentanil, alphacetyhnethadol, alphaprodine, alprazolam, amobarbital, amphetamine, anileridine, apomorphine, aprobarbital, barbital, barbituric acid derivative, bemidone, benzoylecgonine, benzphetamine, betacetylmethadol, betaprodine, bezitramide, bromazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecgonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethadol, levomethadone, levomethadyl acetate, levomethorphan, levorphanol, lofentanil, loperamide, loprazolam, lorazepam, lormetazepam, lysergic acid, lysergic acid amide, mazindol, medazepam, mefenorex, meperidine, meptazinol, metazocine, methadone, methamphetamine, methohexital, methotrimeprazine, methyldihydromorphinone, methylphenidate, methylphenobarbital, metopon, morphine, nabilone, nalbuphine, nalbupine, nalorphine, narceine, nefopam, nicomorphine, nimetazepam, nitrazepam, nordiazepam, normethadone, normorphine, oxazepam, oxazolam, oxycodone, oxymorphone, pentazocine, pentobarbital, phenadoxone, phenazocine, phencyclidine, phendimetrazine, phenmetrazine, pheneridine, piminodine, prodilidine, properidine, propoxyphene, racemethorphan, racemorphan, racemoramide, remifentanil, secobarbital, sufentanil, talbutal, thebaine, thiamylal, thiopental, tramadol, trimeperidine, vinbarbital, allobarbitone, alprazolam, amylobarbitone, aprobarbital, barbital, barbitone, benzphetamine, brallobarbital, bromazepam, brotizolam, buspirone, butalbital, butobarbitone, butorphanol, camazepam, captodiame, carbromal, carfentanil, carpipramine, cathine, choral, chloral betaine, chloral hydrate, chloralose, chlordiazepoxide, chlorhexadol, chlormethiazole edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, enciprazine, estazolam, ethyl loflazepate, etizolam, febarbamate, fencamfamin, fenfluramine, fenproporex, fluanisone, fludiazepam, flunitraam, flunitrazepam, flurazepam, flutoprazepam, gepirone, glutethimide, halazepam, haloxazolam, hexobarbitone, ibomal, ipsapirone, ketazolam, loprazolam mesylate, lorazepam, lormetazepam, mazindol, mebutamate, medazepam, mefenorex, mephobarbital, meprobamate, metaclazepam, methaqualone, methohexital, methylpentynol, methylphenobarbital, midazolam, milazolam, morphine, nimetazepam, nitrazepam, nordiazepam, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibarbal, quazepam, quinalbaritone, secobarbital, secbutobarbitone, sibutramine, temazepam, tetrazepam, triazolam, triclofos, zalepan, zaleplon, zolazepam, zolpidem, and zopiclone.

4. The composition of claim 3 wherein the drug prone to abuse is selected from the group consisting of oxycodone, oxymorphone, hydrocodone, hydromorphone, morphine, tramadol, methylphenidate, and amphetamine.

5. The composition of claim 4 wherein the drug prone to abuse is oxycodone.

6. The composition of claim 1 wherein the fatty acid has a chain length of $C_5$ to $C_{30}$.

7. The composition of claim 1 wherein one or more carrier materials is a wax or a wax-like substance.

8. The composition of claim 7 wherein the wax is selected from the group consisting of beeswax, glycowax, castor wax, carnauba wax, paraffins, and candelilla wax.

9. The composition of claim 1, wherein the drug prone to abuse is oxycodone, the fatty acid has a chain length of $C_5$ to $C_{30}$, and one or more carrier materials is a wax selected from the group consisting of beeswax, glycowax, castor wax, carnauba wax, paraffins, and candelilla wax.

10. The composition of claim 1, wherein the microparticles are further formulated into a tablet or capsule for oral administration.

11. The composition of claim 9, wherein the microparticles are further formulated into a tablet or capsule for oral administration.

* * * * *

UNITED STATES PATENT AND TRADEMARK OFFICE
CERTIFICATE OF CORRECTION

PATENT NO. : 9,044,398 B2  
APPLICATION NO. : 13/551455  
DATED : June 2, 2015  
INVENTOR(S) : Hirsh et al.

Page 1 of 1

It is certified that error appears in the above-identified patent and that said Letters Patent is hereby corrected as shown below:

Title Page, Item (75) Inventors, should read

-- (75) Inventors: Jane Hirsh, Wellesley, MA (US); Alexander M. Klibanov, Newton, MA (US); Alison Fleming, Marshfield, MA (US); Roman V. Rariy, Allston, MA (US) --.

Signed and Sealed this  
Twenty-fourth Day of November, 2015

Michelle K. Lee  
*Director of the United States Patent and Trademark Office*